(12) United States Patent
Yu et al.

(10) Patent No.: US 9,206,118 B2
(45) Date of Patent: Dec. 8, 2015

(54) SULFATED PSYLLIUM DERIVATIVE FOR REDUCING THE RISK OF CHRONIC HUMAN DISEASES AND METHOD FOR PREPARING THE SAME

(75) Inventors: Liangli Yu, Ellicott City, MD (US); Wei Liu, Jiangsu (CN); Zhouhong Xie, Greenbelt, MD (US); Qin Wang, Savoy, IL (US); Boce Zhang, Beijing (CN)

(73) Assignee: University of Maryland, College Park, College Park, MD (US)

( * ) Notice: Subject to any disclaimer, the term of this patent is extended or adjusted under 35 U.S.C. 154(b) by 753 days.

(21) Appl. No.: 12/847,747

(22) Filed: Jul. 30, 2010

(65) Prior Publication Data

US 2011/0054207 A1    Mar. 3, 2011

Related U.S. Application Data

(60) Provisional application No. 61/230,929, filed on Aug. 3, 2009.

(51) Int. Cl.
| | |
|---|---|
| *A61K 36/68* | (2006.01) |
| *C07C 303/00* | (2006.01) |
| *C07C 303/26* | (2006.01) |
| *A23L 1/30* | (2006.01) |
| *C07C 303/44* | (2006.01) |

(52) U.S. Cl.
CPC .............. *C07C 303/26* (2013.01); *A23L 1/3002* (2013.01); *C07C 303/44* (2013.01); *A23V 2002/00* (2013.01)

(58) Field of Classification Search
CPC . A61K 2300/00; A61K 45/06; A61K 36/736; A61K 47/36; A61K 36/28; A61K 2236/00; A61K 2236/10
See application file for complete search history.

(56) References Cited

U.S. PATENT DOCUMENTS

| | | | |
|---|---|---|---|
| 4,321,263 | A | 3/1982 | Powell et al. |
| 6,248,373 | B1 | 6/2001 | Yu et al. |

FOREIGN PATENT DOCUMENTS

WO    2007/087583 A2    8/2007

OTHER PUBLICATIONS

Vogl et al. (2000) Carbohydrate Polymers 41: 185-190.*
Arjmandi B. H., Craig J., Nathani S., Reeves R. D.; "Soluble dietary fiber and cholesterol influence in vivo hepatic and intestinal cholesterol biosynthesis in rats"; Journal of Nutrition, 1992; 122:1559-1565.
Dodgson,K. S., Price, R. G.; "A note on the determination of the ester sulphate content of sulphated polysaccharides" Biochem. J. 84, 106-110 (1962).
Allen, K.G.D., Bristow, S.J. and Yu, L.; "Hypolipidemic effects of modified psyllium preparations"; J. Agric. Food Chem. 52: 4998-5003, 2004.
Baljit Singh, G. S. Chauhan, S. Kumar, Nirmala Chauhan; Synthesis, characterization and swelling responses of pH sensitive psyllium and polyacrylamide based hydrogels for the use in drug delivery (I); Carbohydrate Polymers 67: 190-200.
Kumar K, Verma M; "Functionalization of psyllium with methacrylic acid through grafting and network formation for use of polymers in water treatment"; Journal of Applied Polymer Science 103, 1025-1034, 2007.
Yu, L; Perret, J. "Effects of xylanase treatment on gelling and water-uptaking properties of psyllium"; J. Agric. Food Chem. 2003, 51, 492-495.
Chan, et al., "A forgotten natural dietary fiber: Psyllium mucilloid"; Cereal Food World; 1988; vol. 33, No. 11, pp. 919-992.
Cheng, Z., Blackford, J., Wang, Q., Yu L. 2009; "Acid treatment to improve psyllium functionality"; Journal of Functional Foods. 1: 44-49.
Saghir, et al.; "Structure characterization and carboxymethylation of arabinoxylan isolated from Ispaghula (Plantago ovata) seed husk, Carbohydrate Polymers", vol. 74, Issue 2, Oct. 16, 2008, pp. 309-317.
Saghir, et al.; "Ethylation of arabinoxylan from Ispaghula (Plantago ovata) seed husk"; Carbohydrate Polymers vol. 77, Issue 1, May 22, 2009, pp. 125-130.

* cited by examiner

*Primary Examiner* — Chris R Tate
*Assistant Examiner* — Russell Fiebig
(74) *Attorney, Agent, or Firm* — Rosenberg, Klein & Lee

(57) ABSTRACT

The invention is directed to a method for preparing sulfated psyllium derivatives for use to reduce the risk of chronic human diseases. The sulfation of psyllium was carried out with sulfur, trioxide, pyridine, dimethylformamide and chlorosulfonic acid in pyridine. Six total sulfated psyllium derivatives named SP1, SP2, SP3, SPR1, SPR2, and SPR3 were prepared and evaluated for their morphological and rheological properties, and bile acid-binding abilities. The invention offers a novel approach to obtaining sulfated psyllium derivatives for use in functional foods or supplemental and pharmaceutical products to increase health benefits.

14 Claims, 12 Drawing Sheets

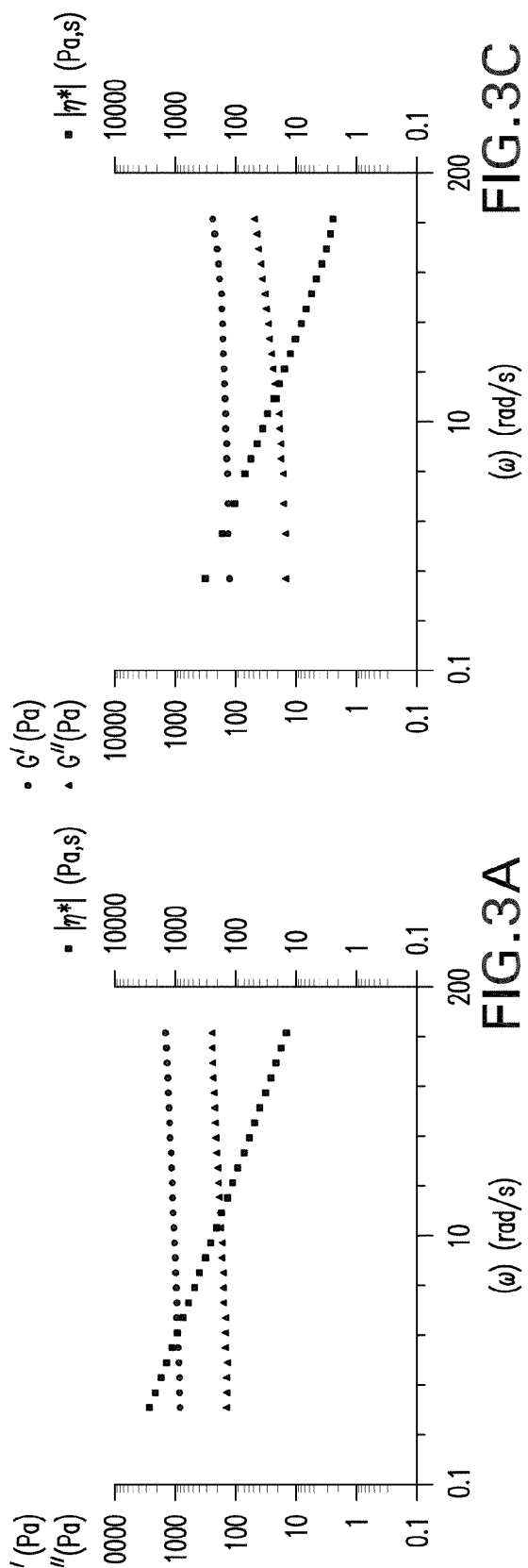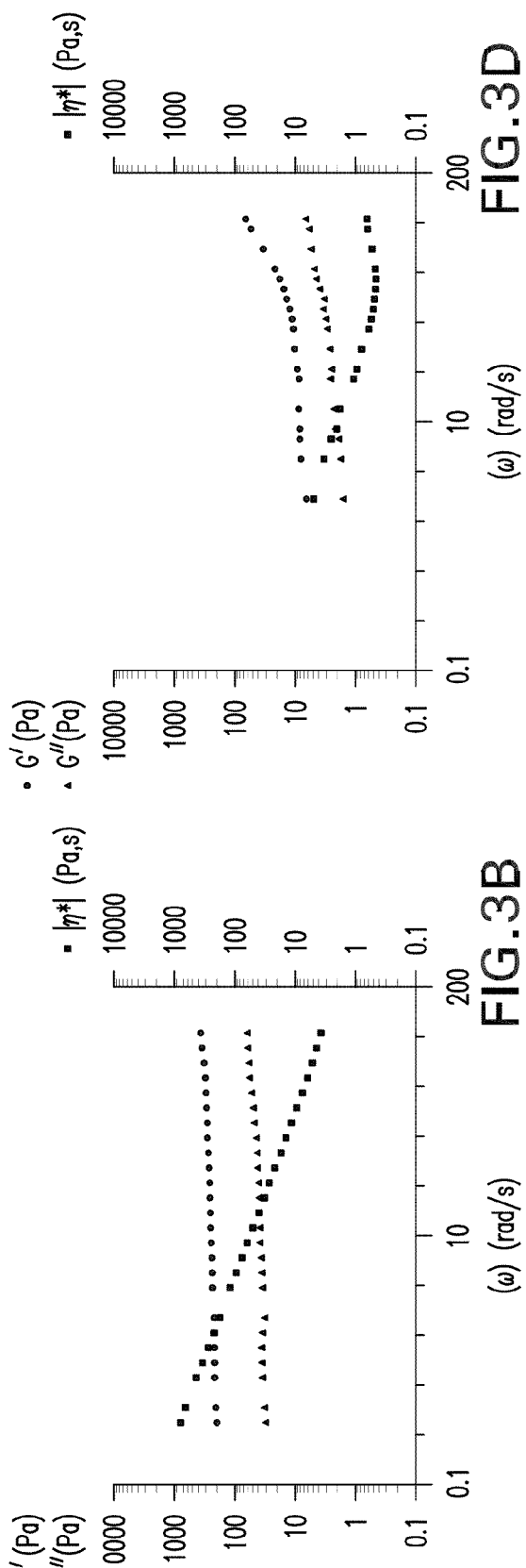
FIG.3A  FIG.3B  FIG.3C  FIG.3D

SULFATED PSYLLIUM DERIVATIVE FOR REDUCING THE RISK OF CHRONIC HUMAN DISEASES AND METHOD FOR PREPARING THE SAME

CROSS-REFERENCE TO RELATED APPLICATIONS

This Application claims priority under 35 U.S.C. §119(e) from U.S. Provisional Patent Application Ser. No. 61/230,929 filed 3 Aug. 2009 which is incorporated in its entirety by reference herein.

FIELD OF THE INVENTION

The present invention relates to methods for improving the physiochemical and functional properties of psyllium through sulfation. The modified psyllium produced by these processes exhibits a reduced gelling capacity of psyllium, reduced viscosity, and increases in bile acid-binding capacity. Accordingly, the sulfation of psyllium is a novel approach for obtaining derivatives having desirable physiochemical, functional, and biological properties for utilization in the nutritional supplement, pharmaceutical, food, nutrition, and homeopathic medicinal industries.

BACKGROUND OF THE INVENTION

This invention pertains to the modification of psyllium, and in particular, to the sulfation of psyllium. More specifically, psyllium is a mucilaginous material prepared from the seed husks of the plants of the *Plantago* genus. The genus including *Plantago* contains over 200 species, including but not limited to *P. ovata* and *P. psyllium*, which are grown commercially in several European countries as well as in parts of Asia including Pakistan and India.

Psyllium possesses many physiological activities such as a hypolipidemic effect, reducing risks associated with colon cancer, reducing hyperglycemia, body weight control, and treatments for irritable bowel syndrome, constipation, and gastric hypoacidity (Arjmandi, et al., (1992) *J. Nutr.* 122: 1559-1565; Allen, et al., (2004) *J. Agric. Food Chem.* 52:4998-5003). Further research has also discovered that psyllium is useful in drug delivery systems, cosmetic products and the processes associated with water treatment (Baljit, et al., (2007) *Carbohydr. Polym.* 67:190-200; PCT Application Publication WO2007/087583; Kumar, et al., (2007) *J. Appl. Polym. Sci.* 103:1025-1034). Of the more than 200 *Plantago* species, the preferred species is *Plantago ovata*, which is commercially grown in India. The mucilage polysaccharide of *P. ovata* is a highly branched acidic arabinoxylan (Yu, et al., (2003) *J. Agric. Food Chem.* 51:492-495; U.S. Pat. No. 6,248,373). The xylan backbone has both (1→4) and (1→3) linkages. Other monosaccharides present in psyllium include D-rhamnose, D-galactose, D-galacturonic acid, 4-O-methyl-D-glucoronic acid, and 2-O-(2-D-galactopyrano syluronic acid)-L-rhamnose (Chan, et al., (1998) *Cereal Foods World* 33:919-992).

Notwithstanding all of the health added benefits of psyllium, major challenges still exist in finding effective ways to incorporate psyllium into food and beverage formulas or in dietary supplements and/or other consumer products at the level required for increased health effects. These challenges exist in large part due to the physiochemical properties of psyllium. These physiochemical properties include, but are not limited to, its high viscosity, its strong gelling capacity when placed in aqueous systems, and its strong water absorbing capacity. Due to the strong hydrophilic and gelling properties of psyllium it is difficult to incorporate psyllium in a food or beverage formula because a substantial amount of time is required for complete dispersal and miscibility of psyllium in an aqueous system containing other ingredients, including sugar, even when the aqueous solution is vigorously agitated. An unpleasant slimy mouth feel and undesirable flavor characteristics are also properties associated with psyllium and properties which can be recognized in foods wherein psyllium is an ingredient. Beverages are the preferred carrier of nutraceuticals, however, adding the recommended amount of psyllium into a beverage becomes nearly impossible due to the hydrophilic and gel forming capacity of psyllium.

It is well accepted that the physiological and functional properties of psyllium are highly dependent on their physiochemical properties, which are determined by their molecular and chemical structures. Accordingly, there has been a growing need to provide a method for modifying the physiochemical and functional properties of psyllium such that the less desirable properties of psyllium are diminished and the more desirable effects of psyllium, such as bile acid-binding abilities and other associated health added benefits are simultaneously enhanced. To promote the application of psyllium in foods or other consumer products, it is necessary to improve the functional/biological and physiochemical properties.

PRIOR ART

Physical, mechanical, enzymatic, and chemical approaches have been developed to improve the physiochemical properties of psyllium and consequently to promote its utilizations in food and other consumer products (Powell, et al., U.S. Pat. No. 4,321,263; Yu, et al. (2003) *J. Agric. Food Chem.* 51: 492-495; Yu, et al., U.S. Pat. No. 6,248,373; and Cheng, et al., *J. Functional Food I.* (2009) 44-49).

The primary limitations related with the enzymatic modification of psyllium are the availability of food grade enzymes and the processing costs associated therewith. Notwithstanding these limitations, however, enzymatic approaches do not involve or generate organic solvents and chemicals and are generally considered "green" (Yu, et al., 2001; Yu, et al. 2003; Cheng, et al. 2009).

In contrast to the use of enzymatic modifications to psyllium, chemical modifications are less expensive and may produce a larger variety of effective derivatives. For example, carboxymethylated arabinoxylan was successfully prepared from the arabinoxylan isolated from psyllium seed husks of the *Plantago ovata* plant by reacting the seed husks with sodium monochloroacetate under a strong alkaline conditions. The carboxymethylation effectively enhances the water solubility of the arabinoxylan from psyllium (Saghir, et al. (2008) *Carbohydr. Polym.* 74:309-317). Further still, ethylation of psyllium arabinoxylan was successfully achieved using ethyl iodide and sodium hydroxide in the presence of methanol, ethanol, or acetone. Ethylation effectively altered the intrinsic viscosity of the arabinoxylan derivatives (Saghir, et al. (2009) *Carbohydr. Polym.* 77:125-130). Further improvements using the chemical methods discussed when the treatment with ethanol solution of hydrochloric acid was shown to improve the functionality of psyllium by reducing its gelling, water uptake, and swelling capacities (Cheng, et al. 2009).

Additionally, it has been shown that grafting and cross-linking methods were able to enhance the efficacy of modified psyllium for application in drug delivery devices. As such, the potential for improving psyllium functionality through chemical modifications exists.

SUMMARY OF THE INVENTION

It is an object of the present invention to provide a method for synthesizing sulfated psyllium derivatives through various chemical modifications.

It is another object of the present invention to provide a method for synthesizing sulfated psyllium derivatives using sulfur trioxide-pyridine ($SO_3.Py$) as a sulfating agent.

It is further object of the present invention is to provide a method for synthesizing sulfated psyllium derivatives using chlorosulfonic acid ($ClSO_3H$) as a sulfating agent.

It is a further object of the present invention to provide a method for synthesizing sulfated psyllium derivatives that will produce a sulfated psyllium derivative having an increased bile acid-binding capacity.

It is yet another object of the present invention to provide a method for synthesizing sulfated psyllium derivatives that will produce a sulfated psyllium derivative having a reduced viscosity when placed in an aqueous system.

It is a further object of the present invention to provide a method for synthesizing sulfated psyllium derivatives that will produce a sulfated psyllium derivative having a reduced gelling capacity.

It is another object of the present invention to provide a method for synthesizing sulfated psyllium derivatives that produce a sulfated psyllium derivative useful in functional foods, and/or supplemental and pharmaceutical products.

It is another object of the present invention to provide a method for synthesizing sulfated psyllium derivatives that will produce a sulfated psyllium derivative having the ability to assist in weight loss, function as a laxative, and lower blood cholesterol levels.

In overall concept, the method for preparing sulfated psyllium derivatives includes preparing an effective amount of a sample of psyllium from raw psyllium through acid hydrolysis treatment. Following acid hydrolysis of the psyllium, an effective amount of a psyllium sample is soaked in an effective amount of a first organic solvent for forming a first mixture. Further, an effective amount of a sulfating agent is dissolved in an effective amount of a second organic solvent for forming a second mixture. The first and second mixtures are then blended, each into the other, for initiating a reaction and forming a reaction mixture. After predetermined reaction conditions have been satisfied, the reaction is terminated with an effective amount of water. Upon termination of the reaction, the reaction mixture is neutralized with an effective amount of a basic solution and a sulfated psyllium derivative is isolated by precipitating the neutralized mixture.

In another embodiment a sulfated psyllium derivative is prepared by preparing an effective amount of a first sample of psyllium from raw psyllium through acid hydrolysis treatment and soaking the said sample of psyllium in an effective amount of dry dimethylformamide (dDMF) for forming a first mixture. An effective amount of sulfur trioxide pyridine complex ($SO_3.Py$) is dissolved in an effective amount of a dimethylformamide (DMF) for forming a second mixture. The first and second mixtures are blended, each into the other, for initiating a first reaction and forming a first reaction mixture. After predetermined reaction conditions have been satisfied, the first reaction is terminated with an effective amount of water. Upon termination of the first reaction, the first reaction mixture is neutralized with an effective amount of sodium hydroxide for formation of a first neutralized mixture. The first neutralized mixture is centrifuged and a first precipitated mixture is obtained having a first precipitate and a first supernatant. The first precipitate is separated from the first supernatant and the first supernatant is set aside for further use.

The method further calls for soaking a second sample of psyllium in an effective amount of dry dimethylformamide (dDMF) for forming a third mixture. An effective amount of sulfur trioxide pyridine complex ($SO_3.Py$) is dissolved in an effective amount of a dimethylformamide (DMF) for forming a fourth mixture. The third and fourth mixtures are blended, each into the other, for initiating a second reaction and forming a second reaction mixture. After predetermined reaction conditions have been satisfied, the second reaction is terminated with an effective amount of water. Upon termination of the second reaction, the second reaction mixture is neutralized with an effective amount of sodium hydroxide for formation of a second neutralized mixture. The second neutralized mixture is centrifuged and a second precipitated mixture is obtained having a second precipitate and a second supernatant. The second precipitate is separated from the second supernatant and the second supernatant is set aside for further use.

The method then calls for blending the first supernatant into second supernatant for obtaining a combined supernatant. A sulfated psyllium derivative is isolated by precipitating the combined supernatant.

It is yet another object of the present invention to provide for a psyllium derivative for use in functional foods, supplemental products, and pharmaceutical products comprising psyllium and at least one sulfonic group bonded to an outer surface area of said psyllium through reaction with a sulfating agent.

These and other objects of the present invention will become apparent when considered in view of further description accompanying the patent drawings.

BRIEF DESCRIPTION OF THE DRAWINGS

FIGS. 3A-3D are graphical representations illustrating the effects of sulfation on the G', G'', and $\eta^*$ with frequency ($\omega$) of Psy, SP1, SP2, and SP3;

DETAILED DESCRIPTION OF THE PREFERRED EMBODIMENTS

Figure 1:
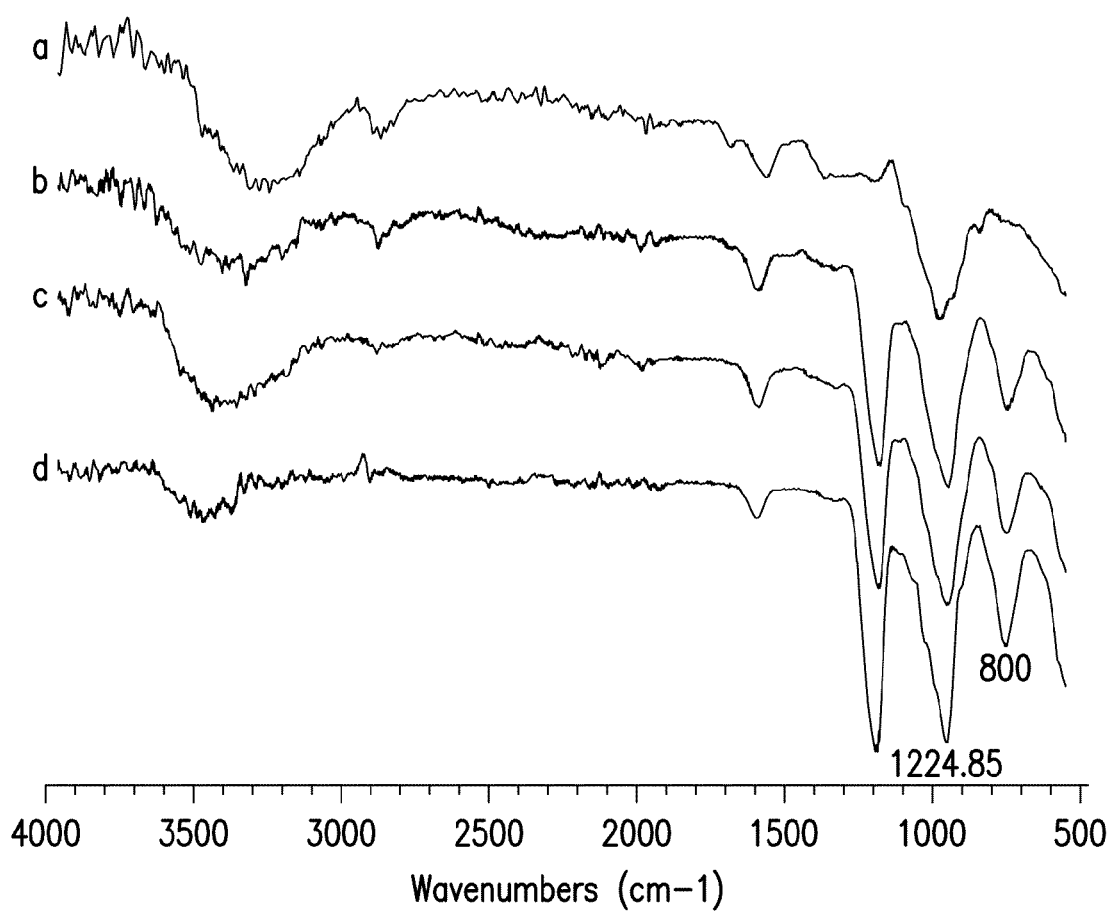
FIG. 1 is a graphical representation illustrating the IR results of starting psyllium preparation and sulfated psyllium derivatives wherein each of a, b, c, and d represent the starting psyllium preparation (Psy), sulfated psyllium with low sulfur content (SP1), sulfated psyllium with medium sulfur content (SP2), and sulfated psyllium with high sulfur content (SP3), respectively.

In general, the terms and phrases used herein have their art-recognized meaning, which can be found by reference to standard texts, journal references, and context known to those skilled in the art. The following definitions are provided to clarify their specific use in context of the disclosure.

"Raw psyllium" as used herein is intended to include, but not be limited to, psyllium husks or any other product that contains psyllium husks or is derived from psyllium husks. This may include whole psyllium seed, psyllium flower, isolated psyllium husk polysaccharides, such as the soluble or insoluble fibers, or mixtures thereof.

"Starting psyllium preparation" as used herein is intended to include acid treated raw psyllium by acid hydrolysis.

"Sulfated psyllium derivative" as used herein is intended to refer to any starting psyllium preparation prepared through sulfation.

"Sulfation" as used herein is intended to include the addition of sulfate groups as esters to a molecule by a sulfating reagent wherein the sulfating reagent may include, but is not limited to, sulfur trioxide-pyridine ($SO_3.Py$) or chlorosulfonic acid ($ClSO_3H$).

General Procedure for the Preparation of Sulfated Psyllium Derivatives

A psyllium sample is obtained from psyllium husks for use as a psyllium sample. This psyllium sample may be an acid treated psyllium preparation or a simple raw psyllium sample. An effective amount of the psyllium sample is then placed within an effective amount of a first organic solvent for soaking and obtaining a first mixture. Next, an effective amount of a sulfating agent is then dissolved in an effective amount of a second organic solvent for obtaining a second mixture. The first mixture is then combined with the second mixture for initiation of a reaction. For every mole of sulfating agent used in the reaction, an effective amount of pyridine is added to the reaction mixture. The reaction is continuously stirred at 60° C. for various predetermined times. The reaction is then allowed to cool to room temperature and an effective amount of cold water is added to the mixture to terminate the reaction. The reaction mixture is further neutralized with an effective molar concentration of sodium hydroxide (NaOH) solution. The neutralized reaction mixture is then dialyzed against distilled water, grade precipitated with ethanol, washed with acetone, and dried under nitrogen.

The neutralized reaction mixture is precipitated with an effective amount of cold ethanol. Following precipitation, the neutralized reaction mixture may be centrifuged before the precipitate is collected and re-dissolved in an effective amount of water. The suspension is then transferred to a dialysis membrane tube and subject to dialysis for a predetermined time for the removal salt and other low molecular weight chemicals. The suspension is concentrated to a predetermined final volume under reduced pressure followed by a second precipitation with an effective amount of ethanol. The precipitated solids are collected and washed at least once with an effective amount of ethanol and acetone and further dried under nitrogen to obtain a final sulfated psyllium derivative.

Implementation of the above referenced method will produce a psyllium derivative for use in functional foods, supplemental products, and pharmaceutical products comprising psyllium having at least one sulfonic group bonded to an outer surface area of the psyllium through reaction with a sulfating agent.

EXAMPLES

The following examples are provided for illustrative purposes and are not intended to limit the scope of the invention as claimed herein. Any variations in the exemplified examples which occur to the skilled artisan are intended to fall within the scope of the present invention.

Example 1

A psyllium sample of 2 g was soaked in 40 mL of dry dimethylformamide (dDMF) and then mixed with 36.73 g of the sulfating agent, sulfur trioxide-pyridine ($SO_3.Py$), dissolved in 50 mL of DMF. For every mole of $SO_3.Py$, mL of pyridine was added to the mixture. The reaction was carried out with continuous stirring at 60° C. for 3 hours. After cooling to room temperature, 250 mL of cold water was added to terminate the reaction followed by the addition of 5 M sodium hydroxide (NaOH) solution to neutralize the reaction mixture. The sulfated psyllium was precipitated by adding ethanol (EtOH) to the mixture. The precipitation was re-suspended in 200 mL of water, dialyzed for 72 hours to remove salt and other low molecular weight chemicals, and concentrated to a final volume of approximately 250 mL under reduced pressure, followed by precipitation with 4 volumes of ethanol. The solids were collected, washed with ethanol and acetone three times, and dried under nitrogen to obtain the sulfated psyllium derivative SP1.

Example 2

The experiment as set forth in Example 1 was followed except that the reaction conditions were carried out with continuous stirring at 60° C. for 4 hours to obtain the sulfated psyllium derivative SP2.

Example 3

The experiments as set forth in Examples 1 and 2 were followed and two products, SP1 and SP2, were obtained under the two different reaction times of 3 hours and 4 hours respectively. Following the collection of SP1 and SP2, their respective supernatants were combined and another 4 volumes of EtOH was added to precipitate the remaining carbohydrates of the SP1 and SP2 supernatants. The precipitate was washed and dried pursuant to the experiments of Examples 1 and 2 to obtain a third sulfated psyllium derivative, SP3.

TABLE 1

Sulfur contents and degree of sulfation (DS) of sulfated psylliums measured by two different methods.

| | Sulfur content$_{BCG}$ (%) | $DS_{BCG}$ | Sulfur content$_{EA}$ (%) | $DS_{EA}$ |
|---|---|---|---|---|
| SP1 | 7.49$^a$ ± 0.09 | 0.38 | 10.37$^a$ ± 0.09 | 0.58 |
| SP2 | 11.4$^b$ ± 0.16 | 0.66 | 11.11$^b$ ± 0.03 | 0.63 |
| SP3 | 13.55$^c$ ± 0.16 | 0.84 | 13.11$^c$ ± 0.07 | 0.80 |

Table 1 quantifies the sulfur contents and degree of sulfation (DS) values measured pursuant to the Barium Chloride-Gelatin Method and the Elemental Analysis Method.

Sulfur content determinations were more specifically performed according to a previously described barium chloride-gelatin nephelometry with a few minor modifications and a calibration curve was constructed with sodium sulfate as standards (Dodgson, et al., (1962) *Biochem. J.* 84:106-110). Regarding the second method, the elemental analysis method was carried out using a Perkin-Elmer PE 2400-Series II, CHNS/O analyzer (Perkin-Elmer, USA) to confirm the sulfur content determined by barium chloride-gelatin nephelometry. The degrees of substitution (DSub), which indicated the average number of sulfonic groups attached to a xylose unit, was calculated pursuant to the following equation:

$$DSub = \frac{132 \times \frac{S\%}{32}}{100 - \left(\frac{80}{32} \times S\%\right)}. \qquad \text{Eq. 1}$$

As shown in Table 1, SP2 had a greater sulfur content and DS value than SP1. This indicated that a longer sulfation reaction time is directly proportional to the increases in sulfur content and the degree of sulfation of psyllium. Table 1 also illustrates that SP3 had the greatest sulfur content and degree of sulfation. Specifically, pursuant to the barium chloride-gellatin method, SP1 had a sulfur content of 7.49%±0.09 with a $DS_{BCG}$ of 0.38, SP2 had a sulfur content of 11.40%±0.16 with a $DS_{BCG}$ of 0.66, and SP3 had a sulfur content of 13.55%±0.16 with a $DS_{BCG}$ of 0.84 respectively. Further still, results of the Elemental Analysis show that SP1 had a sulfur content of 10.37%±0.9 and a $DS_{EA}$ of 0.58, SP2 had a sulfur content of 11.11%±0.03 and a $DS_{EA}$ of 0.63, and SP3 had a sulfur content of 13.11%±0.07 and a $DS_{EA}$ of 0.80 respectively.

Referring now to FIG. 1, starting psyllium sample Psy and sulfated derivatives SP1, SP2, and SP3 were examined for sulfur content determination using Fourier transform-infrared spectroscopy (FT-IR) and surface charge potential (ζ-potential). FT-IR spectra was recorded on a Thermo Nicolet IR 200 Spectrometer (Thermo, USA).

The surface charge of the particles was characterized by measuring the ζ-potential. The concentration of each of the Psy, SP1. SP2, and SP3 samples solution was 0.1 mg/ml with each sample being mounted to the particle analyzer (Malvern, Zetasizer Nano ZS 90). The output data quantitatively indicated the charge that the particles carried.

FIG. 1 shows the FT-IR spectra of Psy, SP1, SP2, and SP3 having absorption bands ranging from the 400-4000 cm$^{-1}$ wavelength regions. Comparing the starting psyllium preparation, Psy, to the sulfated derivatives, SP1, SP2, and SP3, respectively, it is shown that two new characteristic absorption bands appeared in the FT-IR spectra of the sulfated derivatives, SP1, SP2, and SP3. These bands occurred at approximately the 1224.85 cm$^{-1}$ wavelength. These findings accurately describe the presence of sulfur and more specifically that of an asymmetrical S═O stretching vibration. The other novel absorption band was found at approximately the 800 cm$^{-1}$ wavelength. These findings further indicate the presence of sulfur inasmuch as these novel absorption bands represent a symmetrical C—O—S vibration associated with a C—O—SO$_3$ group. Such a finding indicates the incorporation of the sulfonic groups to sulfated psyllium derivatives SP1, SP2, and SP3. It is also to be noted that the stronger peaks at the approximate wavelengths of 1224.85 and 800 cm$^{-1}$ respectively for SP3 indicate that it has higher sulfur content than SP2, which has higher sulfur content than SP1.

The introduction of the negatively charged sulfonic groups to psyllium molecules was further confirmed by an examination of the surface charge (ζ-potential) for each of SP1, SP2, and SP3 when compared to that of starting sample Psy. Specifically, the ζ-potential of Psy, SP1, SP2, and SP3 were −17.3, −30, −39, and −44.7 mv respectively (results not shown).

FIGS. 2A-2D examines the morphological properties of the starting psyllium preparation, Psy, and the sulfated derivatives, SP1, SP2, and SP3 by scanning electron microscopy (SEM). The comparative results of the SEM results of FIGS. 2-2D clearly show that sulfation has a dramatic impact on the morphology of psyllium.

Figure 2A:
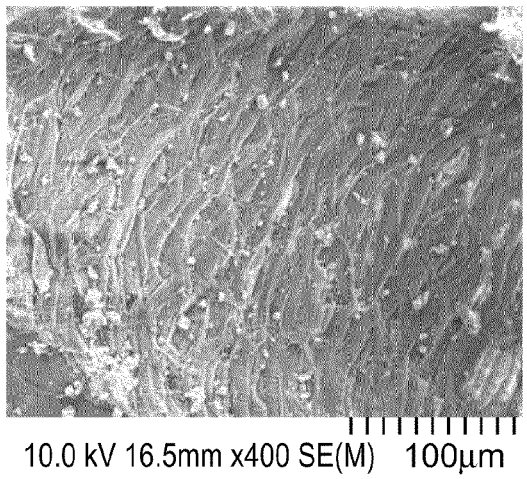
FIGS. 2A-2D are scanning electron microscope measurements Psy (2A), SP1 (2B), SP2 (2C), and SP3 (2D) respectively.
Figure 2B:
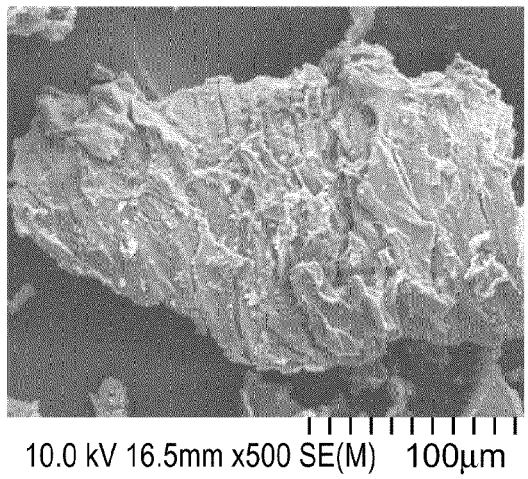
Figure 2C:
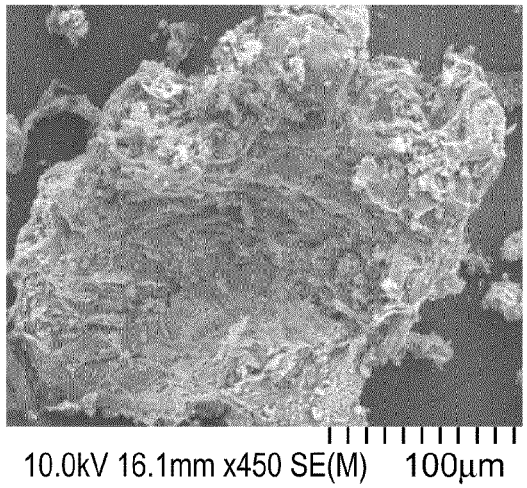
Figure 2D:
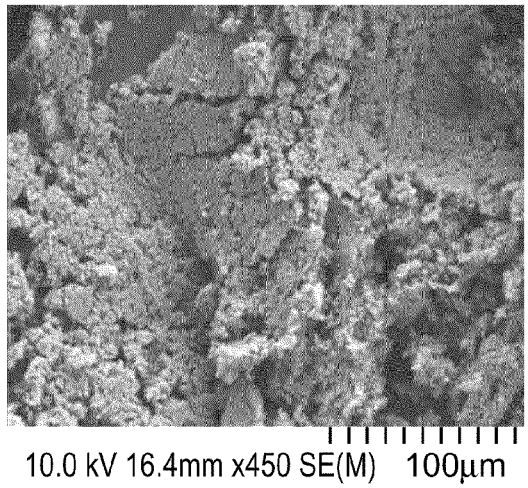

As is shown in FIG. 2A, the starting psyllium sample, Psy, includes filamentous structures containing regular strands forming a network-like structure on the surface of the starting psyllium preparation. In contrast to FIG. 2A, however, the sulfated samples SP1, SP2, and SP3, as shown in FIGS. 2B-2D are markedly less fibrillar. In fact, when comparing the sulfated samples SP1, SP2, and SP3 to the starting psyllium sample Psy, it is clearly illustrated that the surface changes in morphology are directly related to the sulfation of psyllium.

More specifically, the sulfonic groups attached to the psyllium polymer show a less filamentous structure causing an overall reduction in the available surface area of the psyllium. As can be seen in FIGS. 2B-2C, SP1 and SP2 still exhibited some filamentous structure but that structure has been significantly eroded when compared to that of the starting psyllium sample in block a of FIG. 2. Regarding FIG. 2D, SP3 shows mostly a small aggregate of clusters or broken particles and no remnants of the filamentous structure found in the starting sample Psy or the less sulfated samples SP1 and SP2. Further still, the SEM results of FIG. 2 show that sulfation had a profound impact on the overall morphology of psyllium.

Referring now to FIGS. 3A-3D, an examination of the rheological properties of the starting psyllium sample, Psy, and the sulfated derivatives, SP1, SP2, and SP3, were determined using an AR2000ex rheometer (TA Instrument, Leatherhead, UK) to measure the viscoelastic properties of the psyllium samples. Each of the Psy, SP1, SP2, and SP3 samples were dissolved and mixed in water at a concentration of 5 mg/mL. Rheological properties were characterized immediately after each of the Psy, SP1, SP2, and SP3 solutions were prepared at 25±1° C. with a 60 mm 59° steel cone. The shear viscosity was measured at a shear rates ranging from 0.01-100 s$^{-1}$ and the dynamic oscillatory testing was performed as a function of frequency (0.1-1000 rad/s). The mean values of at least two measurements were reported for each of the samples Psy, SP1, SP2, and SP3.

The rheological properties of Psy, SP1, SP2, and SP3 are shown in bar graph form in FIGS. 3A-3D respectively. FIGS. 3A-3D show that during the measurement of rheological properties, the elastic modulus (G') of all samples was higher than that of their intrinsic viscous modulus (G"). This indicates that for each of Psy, SP1, SP2, and SP3, a typical weak gel-like property was consistent among all samples. FIGS. 3A-3D clearly show, however, that as sulfation increases, G' and G" decrease indicating that sulfation decreases the gelling properties of psyllium. As is shown by FIGS. 3A-3D, the data illustrates that Psy had the strongest gel under experimental conditions whereas SP1 had a weaker gel than Psy, SP2 had a weaker gel than SP1 and SP3 had the weakest gel of all observed solutions.

FIGS. 3A-3D also illustrate that the apparent viscosity ($\eta^*$) of Psy and sulfated derivatives SP1, SP2, and SP3 decreases as the shear rate for each sample increases. As is further seen in FIGS. 3A-3D, the sulfated derivatives SP1, SP2, and SP3 have a lower apparent viscosity than that of Psy at the tested shear rating range.

Figure 4:
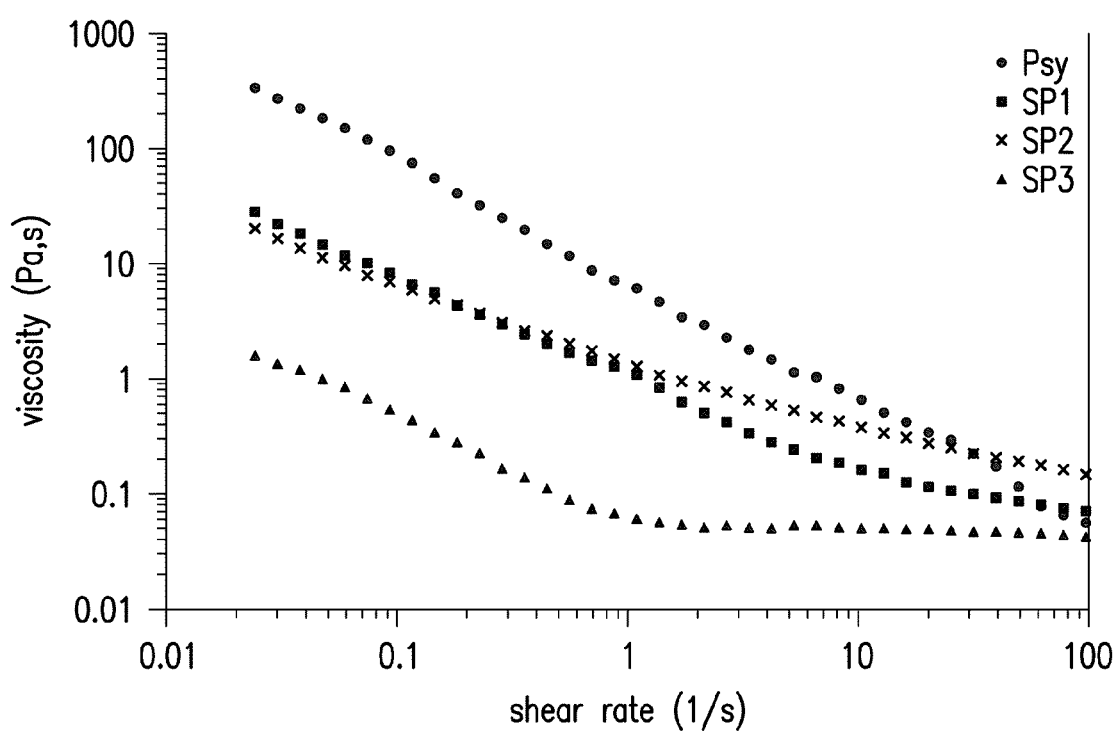
FIG. 4 are graphical representations illustrating the shearing behavior of Psy, SP1, SP2, and SP3.

FIG. 4 is a graphical representation of the shear thinning behavior of psyllium samples Psy, SP1, SP2, and SP3. More specifically, FIG. 4 plots the apparent viscosity versus the shear rate at the double logarithm scale. Specifically, FIG. 4 shows that sulfation derivatives SP1, SP2, and SP3 not only have a substantially lower apparent viscosity but also have a narrower shear thinning region when compared to Psy.

Taken as a whole, the results illustrated in FIGS. 3A-3D and FIG. 4 indicate that sulfate derivatives SP1, SP2, and SP3 have reduced sliminess and will improve the overall mouth feel when sulfated derivatives are used in food products such as breads, crackers and other complex carbohydrate food items. Further still, the data provided in FIGS. 3A-3D and FIG. 4 further indicate that the sulfated psyllium derivatives SP1, SP2, and SP3 will each have superior properties during food processing and consumption when compared to when raw psyllium is used for those purposes.

Figure 5:
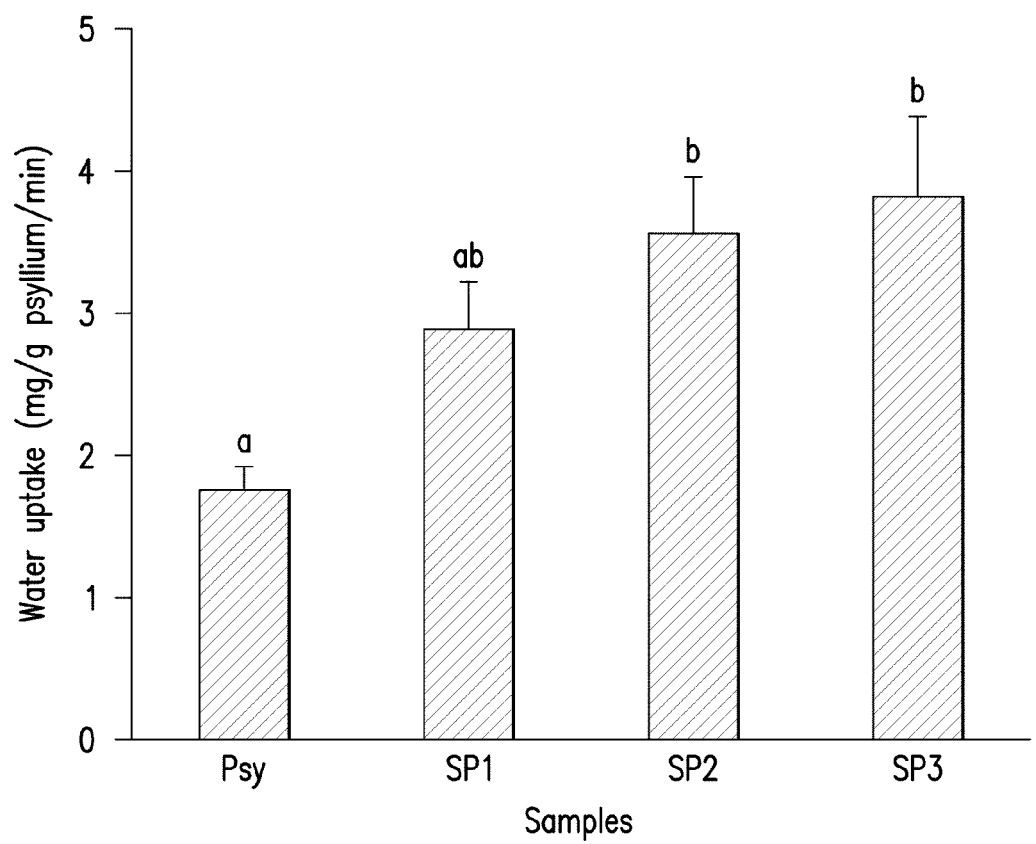
FIG. 5 is a graphical representation of the water uptake capacities of Psy, SP1, SP2, and SP3.

FIG. 5 is a bar graph representation of the effects of sulfation on the water-uptake capacities of psyllium samples Psy, SP1, SP2, and SP3. Measurements were based on a water-uptake capacity assay. Specifically, each of the samples, Psy, SP1, SP2, and SP3, were equilibrated in a 15% relative humidity chamber at ambient temperature (22° C.) for 72 hours. Each of the samples was measured for weight and then transferred to a 90% relative humidity chamber and kept for 30 minutes. Each of the samples was measured again for total weight. The change in weight was calculated and reported as milligrams of water taken by per gram of sample per minute. These results are indicated in FIG. 5.

Figure 6:
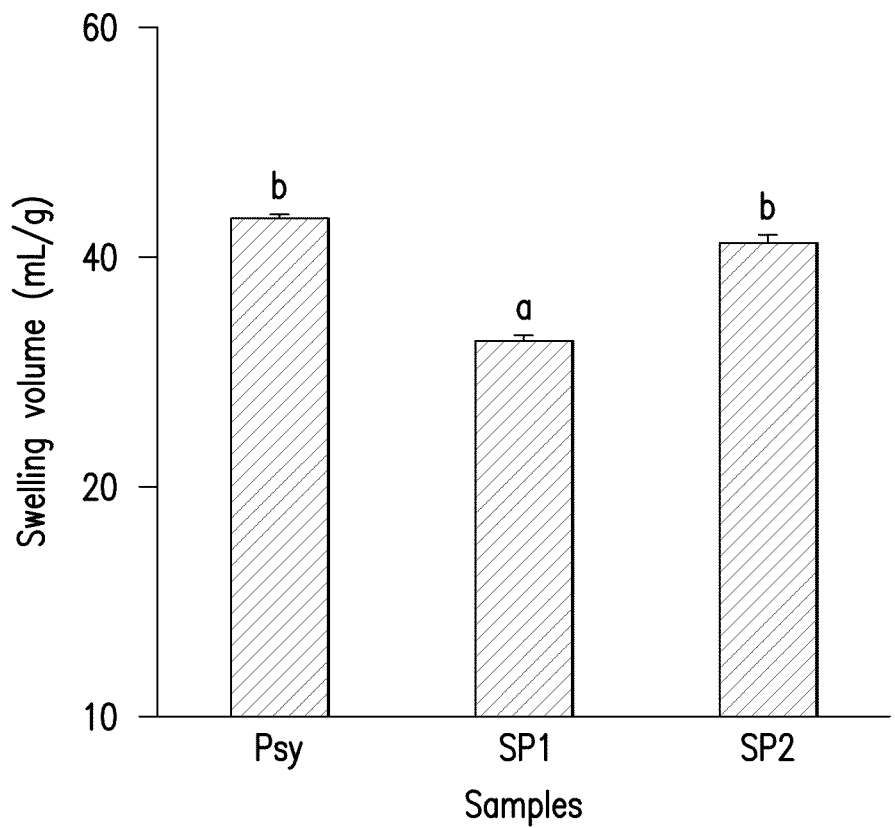
FIG. 6 is a graphical representation of the swelling volume capacity Psy, SP1, SP2, and SP3.

FIG. 6 is a bar graph representation of the effects of sulfation on the swelling volume of psyllium samples Psy, SP1, SP2, and SP3. Swelling capacities of the samples were determined by suspending 0.1 g of each sample in 7 mL of simulated intestinal fluid without enzyme according to U.S. Pharmacopeia. The suspensions were kept at 37° C. for 8 hours with occasional shaking. The mixtures were kept for another 16 hours at ambient temperature (22° C.) for the sediment to settle. The volumes of the sediments were recorded and the swelling capacity was calculated as mL of sediment per g of psyllium sample.

As shown in FIG. 6, SP3 did not form either sediment or gel under the experimental conditions. Each of sulfated psyllium derivatives SP1 and SP2 did form some gelling, however, both sulfated psyllium derivatives had a gelling effect less demonstrable than that of the starting psyllium sample Psy.

As SP3 failed to sediment or form gel under the experimental conditions, and because sulfated psyllium derivatives SP1 and SP2 had swelling volumes less than that of starting psyllium sample Psy, the results indicate that an application for a non-gelling psyllium derivative through sulfation can be obtained.

Figure 7A:
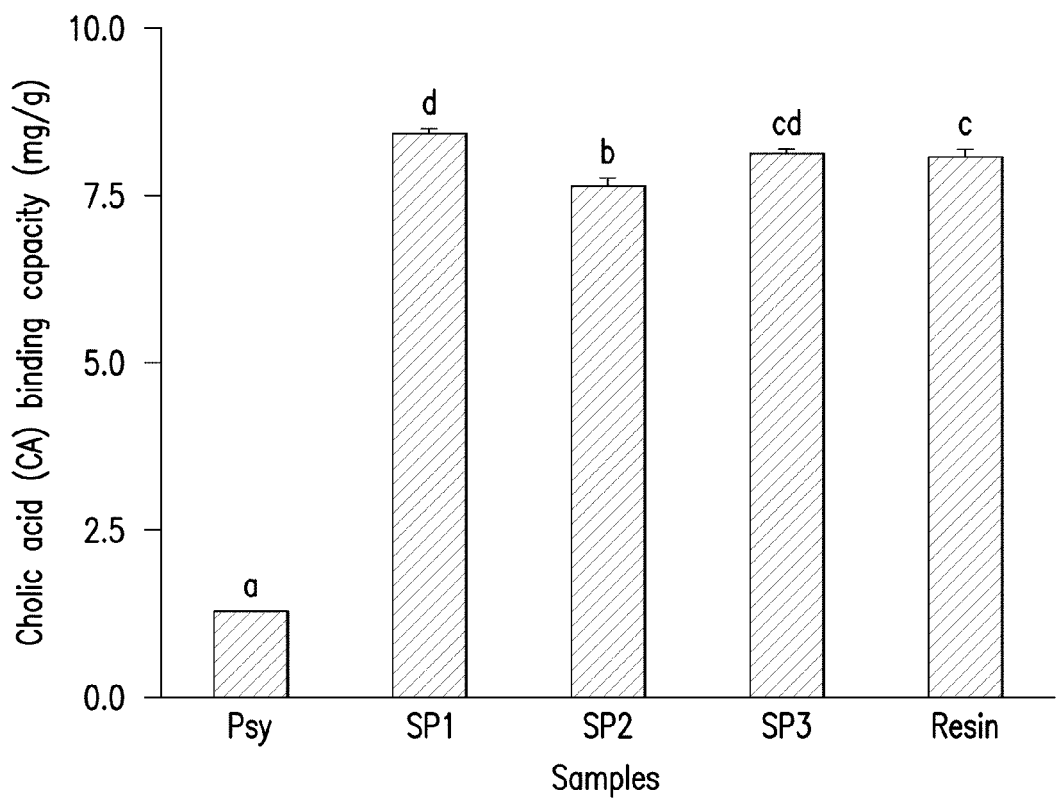
FIGS. 7A-7B are graphical representations of the bile acid-binding capacities of Psy, SP1, SP2, SP3, and resin, wherein resin represents a cholestyramine resin positive control.
Figure 7B:
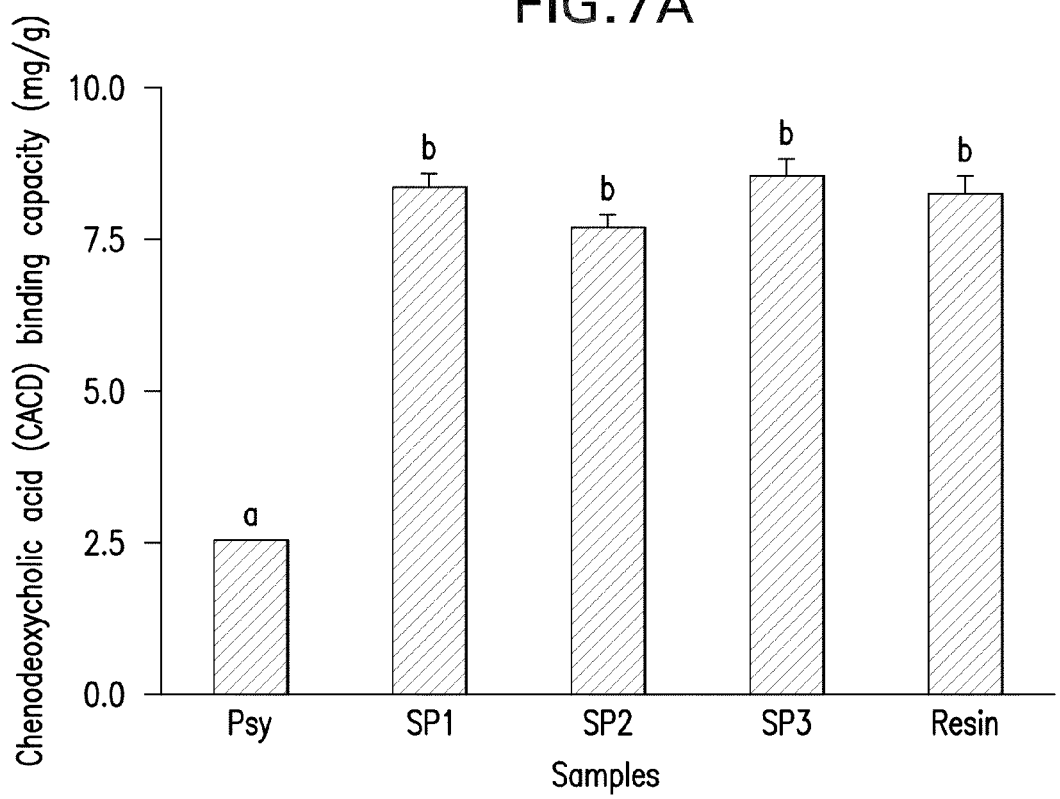

FIGS. 7A and 7B are bar graph representations of the effects of sulfation on the bile acid-binding capacities of psyllium samples Psy, SP1, SP2, and SP3. The bile acid-binding capacities were determined by treating 50 mg of each psyllium sample with 0.5 mL of 0.01 mol/L HCl, which simulated gastric conditions. Each of the samples was incubated at 37° C. for 60 minutes with continuous shaking (50 rpm). The solutions were adjusted to pH 7.0 by adding 0.05 mL of 0.1 mol/L HCl and mixed with 2.5 mL of 400 µmol/L bile acid stock solution prepared in 0.01 mol/L phosphate buffer (pH 7.0) for simulation of intestinal conditions. These mixtures were further incubated for another 60 minutes at 37° C. and then centrifuged for 10 minutes at 6000 rpm. The supernatant was collected for bile acid determination from each of the Psy, SP1, SP2, and SP3 samples respectively.

Quantification of the unbound bile acids was conducted using a commercial kit from Sigma Aldrich (St. Louis, Mo.). The final assay mixture was added with 100 µL of supernatant or bile acid standards, 125 µL of 1.22 mmol/L nicotinamide adenine dinucleotide, 125 µL of 5 mmol/L nitro blue tetrazolium salt, 100 µL of 625 units/L 3-α hydroxysterol dehydrogenase, and 100 µL of 625 units per liter diphorase. The respective mixtures were incubated for 60 minutes at ambient temperature. Following incubation, 100 4 of 1.33 mol/L phosphoric acid was added to terminate the reaction and the absorbance of each reaction mixture was measured at 530 nm indicating the amount of unbound acid.

Phosphate buffer without bile acid was used as a reagent blank and the cholestyramine was used as a positive control to verify the presence of enzyme. The levels of unbound bile acids were obtained using a standard curve prepared with each of the 2 pure bile acids, which were cholic acid (CA) and chenodeoxycholic acids (CACD). The bile acid-binding capacity (mg/g sample) was calculated against a reagent blank. Duplicate tests were performed for each of the Psy, SP1, SP2, and SP3 samples against each bile acid.

As is clearly shown in FIGS. 7A-7B, sulfated psyllium derivatives SP1, SP2, and SP3 had a bile-acid binding capacity significantly greater than that of starting sample Psy. Specifically, FIG. 7A shows that the binding capacity of sulfated derivatives SP1, SP2, and SP3 against cholic acid (CA) was about 8.4 mg/g, 7.6 mg/g, and 8.1 mg/g, respectively. The result obtained for sulfated psyllium samples SP1, SP2, and SP3 are approximately 6.5-fold, 5.9-fold, and 6.3-fold of that of the starting psyllium sample Psy respectively. The acid-binding capacities of sulfated psyllium derivatives SP1, SP2, and SP3 were also significantly greater than that of Psy when tested against chenodeoxycholic acid (CACD) as is seen in FIG. 7B.

Cholestyramine resin was used as a positive control in FIGS. 7A and 7B as it is a quarternary ammonium anion exchange resin with a polystyrene backbone commercially used as an adjunctive therapy for binding bile acids in the intestinal system and reducing plasma control levels. As is clearly shown in FIGS. 7A and 7B, sulfated psyllium derivatives SP1, SP2, and SP3 have a greater efficacy for binding bile acids to polymers which may enhance their elimination and promote the conversion of cholesterol to bile acids. This could have the beneficial effect of reducing plasma total and LDL cholesterol levels as well as the risk for cardiovascular diseases associated therewith. The bar graphical representations of FIGS. 7A and 7B show that sulfation increases bile acid-binding capacity, thus lending for the possible application of sulfated psyllium derivatives as a cholesterol lowering adjutants.

Example 4

5 g of a raw psyllium sample was dispersed into 100 ml, of dDMF and then further mixed with 45.92 g of $SO_3$.Py dissolved in 100 mL of DMF to sulfate the 5 g of psyllium. For every mole of $SO_3.Py$, 1 mL of pyridine was added to the reaction mixture. The reaction mixture was stirred for 4 hours at 60° C., with 250 mL of cold water added to terminate the reaction. Following termination of the reaction, the mixture was neutralized using 5 mol/L NaOH solution. The reaction mixture was then dialyzed against distilled water, grade precipitated with ethanol, washed with acetone, and dried under nitrogen to obtain the sulfated psyllium derivative SRP1.

Example 5

The experiment as set forth in Example 4 was followed except that 91.83 g of $SO_3.Py$ were used to sulfate the 5 g raw psyllium sample to obtain the sulfated psyllium derivative SRP2.

Example 6

5 g of raw psyllium sample were dispersed into 100 mL of DMF and then mixed with 35.42 g of chlorosulfonic acid ($ClSO_3H$) dissolved in pyridine. For every mole of $ClSO_3H$, 1 mL of pyridine was added to the reaction mixture. The reaction mixture was stirred for 4 hours at 60° C. and 250 mL of cold water was added to terminate the reaction. The mixture was neutralized by 5 mol/L NaOH solution. The reaction mixture was dialyzed against distilled water, grade precipitated with ethanol, washed with acetone, and dried under nitrogen.

TABLE 2

Sulfation Reactions for *Psyllium*

| Sample ID | Sulfating Reagent | Ratio of Sulfating Agent (mol/g psyllium) | Yield (%) | Sulfur Content (%) | DS |
|---|---|---|---|---|---|
| SRP1 | $SO_3 \cdot Py$ | 0.057 | 86.7 | 3.05a ± 0.13 | 0.138 |
| SRP2 | $SO_3 \cdot Py$ | 0.115 | 88.6 | 3.15a ± 0.04 | 0.142 |
| SRP3 | $ClSO_3H$ | 0.061 | 93.6 | 13.68b ± 0.40 | 0.858 |

Table 2 quantifies the sulfur contents and degree of sulfation (DS) values measured pursuant to the Barium Chloride-Gelatin Nephelometery Method previously discussed. The degrees of substitution (DSub) which indicated the average number of sulfonic groups attached to a xylose unit was calculated pursuant to Eq. 1 supra.

As is shown in Table 2, SRP2 and SRP1 have similar percentages of sulfur content. Table 2 illustrates that SRP2, prepared with a double concentration of the sulfation agent, did not result in a psyllium derivative having a higher level of sulfation. Additionally, Table 2 makes clear that SRP3 has the greatest sulfur content and degree of sulfation. Specifically, pursuant to the Barium Chloride-Gelatin Method, SRP1 had a sulfur content of 3.05%±0.13 with a DS of 0.138, SRP2 had a sulfur content of 3.15%±0.04 with a DS of 0.142, and SRP3 had a sulfur content of 13.68%±0.40 with a DS of 0.858, respectively.

Table 2 further illustrates that when $ClSO_3H$ was used as a sulfation agent, sulfated psyllium with a higher sulfur content was obtained by using a molar ratio of 61 mmol/g of psyllium—far less than the molar ratios required to obtain the results for SRP1 and SRP2. The $ClSO_3H$ resulted in a sulfated derivative resulting in a sulfur content of 13.68% and a DS value of approximately 0.86. These results indicate that SRP3 has sulfur content approximately 4.5 times greater than that of SRP1 and approximately 4.3 times greater than that of SRP2.

Further still, the results of Table 2 indicate that SRP3 has a DS value approximately 6.2 and 6.0 times greater than SRP1 and SRP2 respectively.

The data in Table 2 shows that $ClSO_3H$ is a very strong sulfation agent for psyllium as psyllium only has limited substitution sites available. Specifically, psyllium primarily contains 1→4 and 1→3 linked β-D-xylopyranosyl residues in its backbone with O-3 and O-2 linkages available for branch chains and sulfonic group substitutions.

Figure 8:
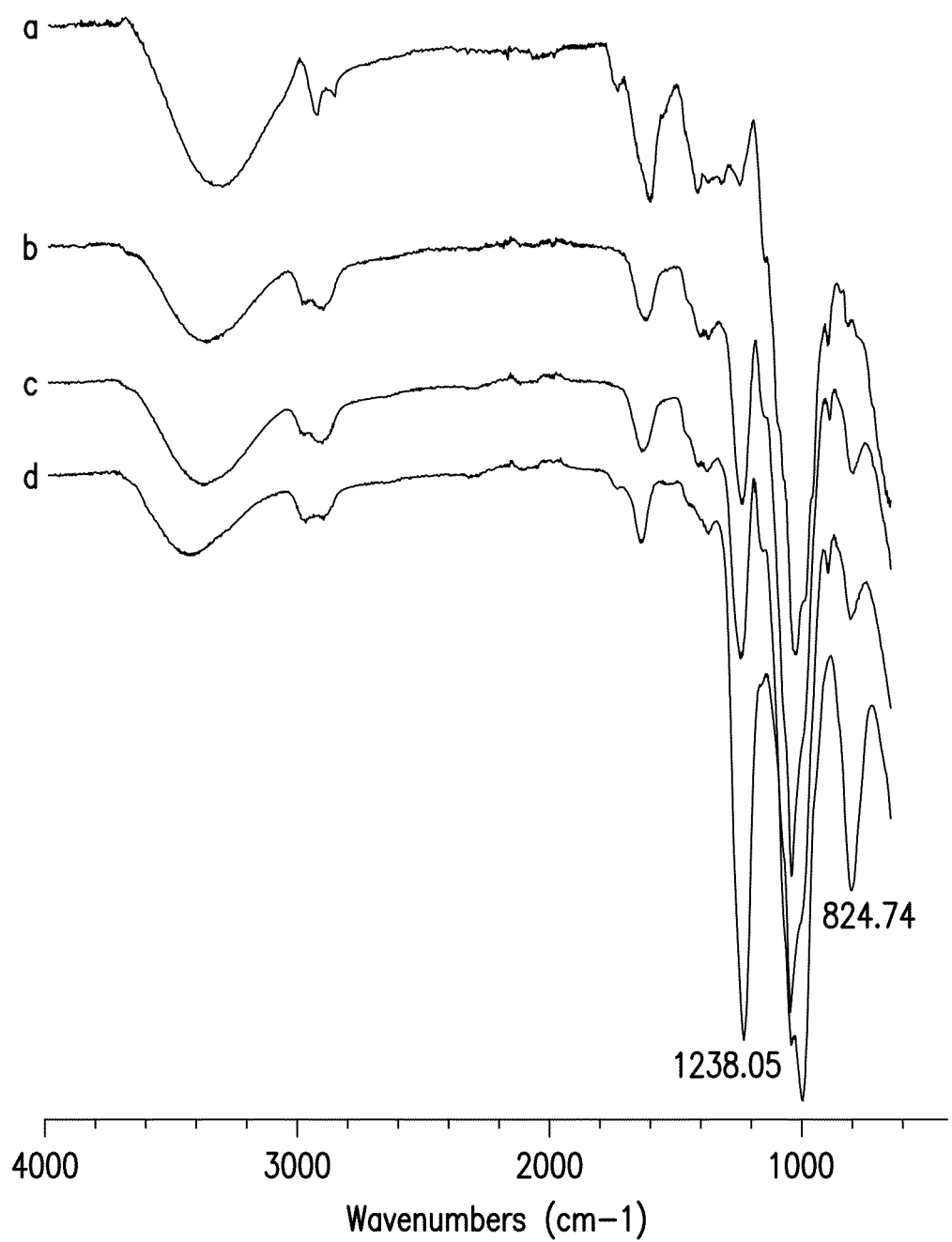
FIG. 8 are graphical representations illustrating the IR results of starting psyllium preparation and sulfated psyllium derivatives wherein each of a, b, c, and d represent the raw psyllium sample (RPsy), the sulfated psyllium with low sulfur content (SRP1), the sulfated psyllium with high sulfur content (SRP2), and the sulfated psyllium using chlorosulfonic acid (SRP3) respectively.

Referring now to FIG. 8, Raw psyllium sample RPsy and sulfated derivatives SRP1, SRP2, and SRP3 were examined for sulfur content determinations using FT-IR as previously discussed. As shown in FIG. 1, FT-IR spectra of RPsy, SRP1, SRP2, and SRP3, have absorption bands extending from the 400-1000 $cm^{-1}$ wavelength regions. Comparing the raw psyllium sample, RPsy, to the sulfated derivatives, SRP1, SRP2, and SRP3, respectively, it is shown that two new characteristic absorption bands appeared in the FT-IR spectra of the sulfated derivatives, SP1, SP2, and SP3. These absorption bands occurred at approximately the 1238.05 $cm^{-1}$ wavelength. Again, these findings accurately describe the presence of sulfur and more specifically that of an asymmetrical S=O stretching vibration. The other novel absorption band was found at approximately the 824.74 $cm^{-1}$ wavelength. Just as with the results of FIG. 1, these findings also indicate the presence of sulfur inasmuch as these novel absorption bands represent a symmetrical C—O—S vibration associated with a C—O—$SO_3$ group. The FT-IR spectra clearly indicate the incorporation of the sulfonic groups to sulfated psyllium derivatives SRP1, SRP2, and SRP3. It should also be noted that the stronger peaks at the approximate wavelengths of 1238.05 and 824.74 $cm^{-1}$ respectively for SRP3 indicate that it has higher sulfur content than SRP2, which has higher sulfur content than SRP1.

Figure 9:
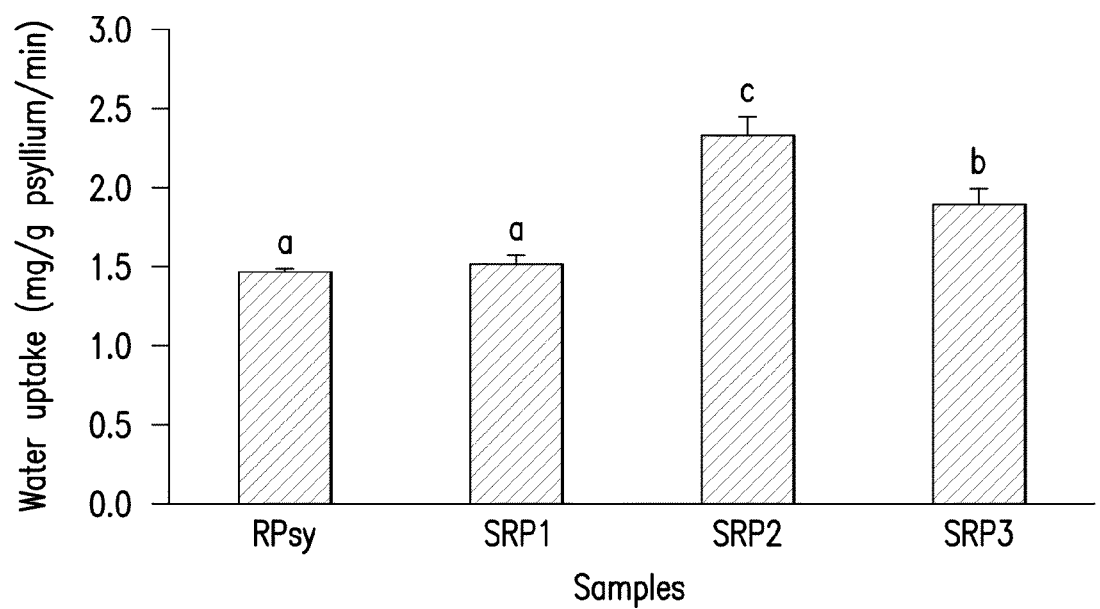
FIG. 9 is a graphical representation of the water uptake capacities of RPsy, SRP1, SRP2, and SRP3.

FIG. 9 is a bar graph representation of the water uptake capacities of raw psyllium, RPsy, and sulfated psyllium derivatives SRP1, SRP2, and SRP3. The method for testing the water-uptake capacity of psyllium and sulfated derivatives thereof is discussed in detail supra.

Figure 10A:
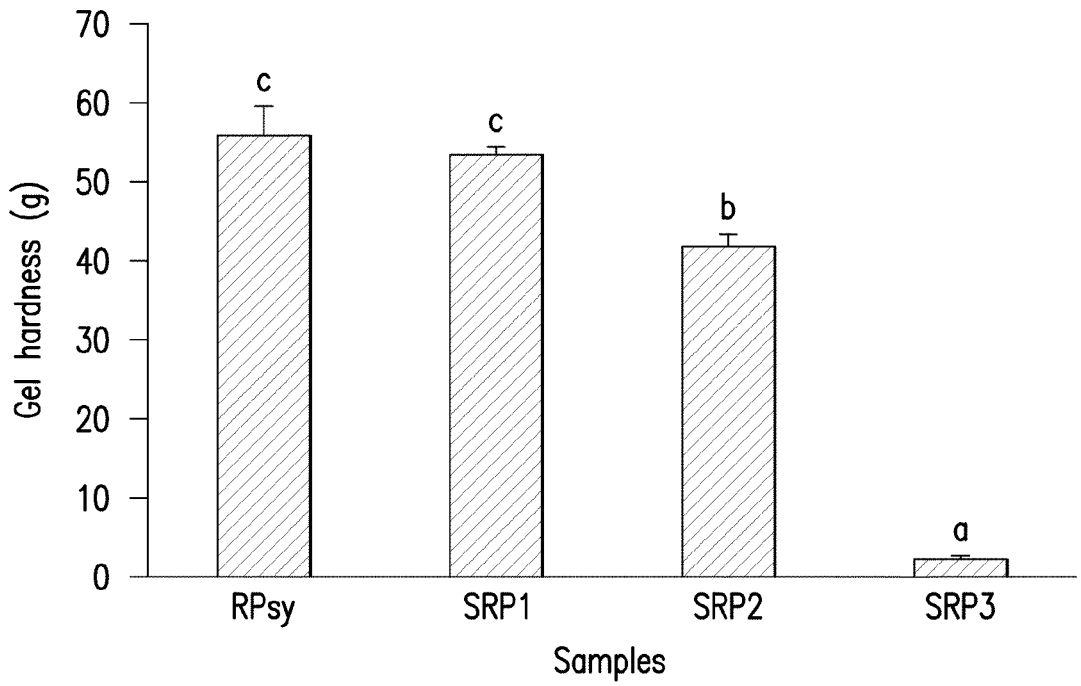
FIGS. 10A-10B are graphical representations of the gelling capacities of RPsy, SRP1, SRP2, and SRP3.
Figure 10B:
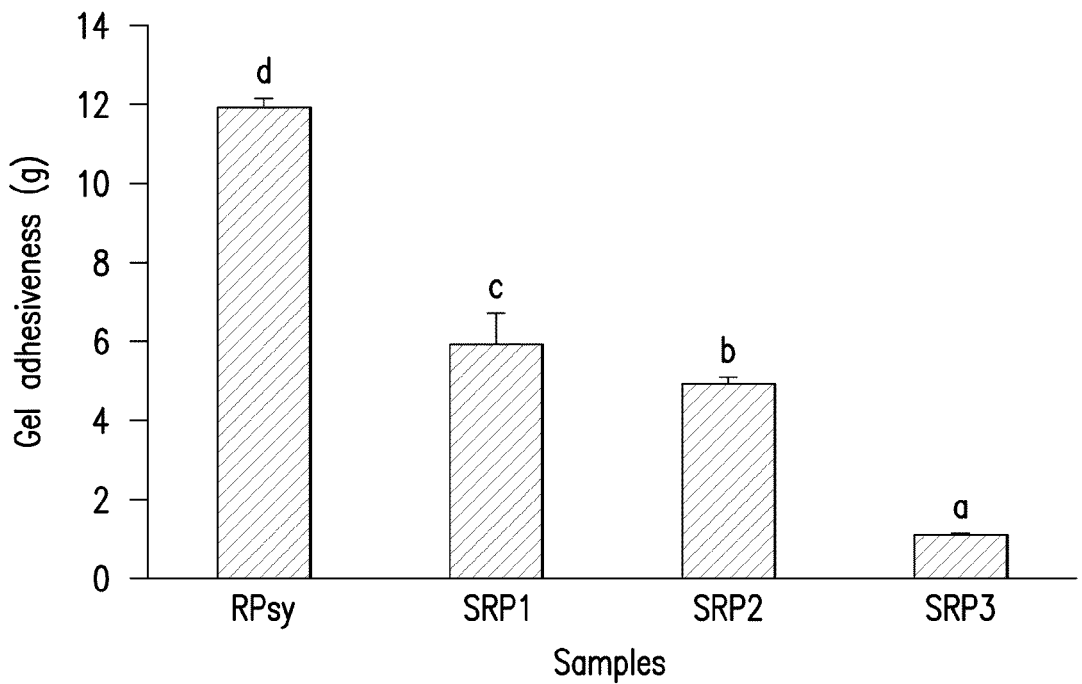

FIGS. 10A and 10B are bar graph representations of the gel hardness and gel adhesiveness of raw psyllium sample RPsy and sulfated psyllium derivatives SRP1, SRP2, and SRP3, respectively. The gelling capacities of the raw psyllium sample RPsy and the sulfated psyllium derivatives SRP1, SRP2, and SRP3 were determined using a TA.XT Plus Texture Analyzer with a 0.5 inch diameter probe (Texture Technologies Corp. Scarsdale, N.Y.).

The gels were prepared by mixing 0.5 g of each of the RPsy, SRP1, SRP2, and SRP3 samples and 10 mL of water in a 50 mL beaker. After allowing each of the respective samples to set for 24 hours at ambient temperature, each gel sample was subjected to a double compression test. The instrumental parameters were set to have a pre-test speed of 2.0 mm/s, a test speed of 5 mm/s, a post-test speed of 5 mm/s, and a test distance of 6 mm. The maximum force necessary to break each gel is determined as the gel hardness and the force exerted by each gel sample to hold the probe was determined as the gel adhesiveness.

As is shown in FIGS. 10A and 10B, the gelling properties as measured by gel hardness in FIG. 10A and gel adhesiveness in FIG. 10B, were lower than the original raw psyllium sample. Specifically, SRP3 showed the lowest values for both gel hardness and adhesiveness. This result indicates that SRP3 has the weakest gel forming capacity of the samples tested. As seen in FIGS. 10A and 10B, sulfated psyllium derivative SRP3 had a gel hardness of 2.5 g and a gel adhesiveness of 0.9 g. FIG. 10A further shows that sulfation via ClSO$_3$H is capable of reducing the gel hardness of SRP3 to 4-5% of that of the raw psyllium sample, RPsy (57 g).

The data provided in FIGS. 10A and 10B shows demonstrably that sulfation is an effective approach to reducing the gelling capacity of psyllium. The data reflected in FIGS. 10A and 10B further indicate that sulfation with ClSO$_3$H improves the efficacy of reducing the gelling capacity of raw psyllium when compared to sulfated derivatives SRP1 and SRP2. Taken together, the results of FIGS. 10A and 10B show that sulfation effectively reduces the gelling capacity of psyllium and thereby improves the functional properties of psyllium.

Figure 11:
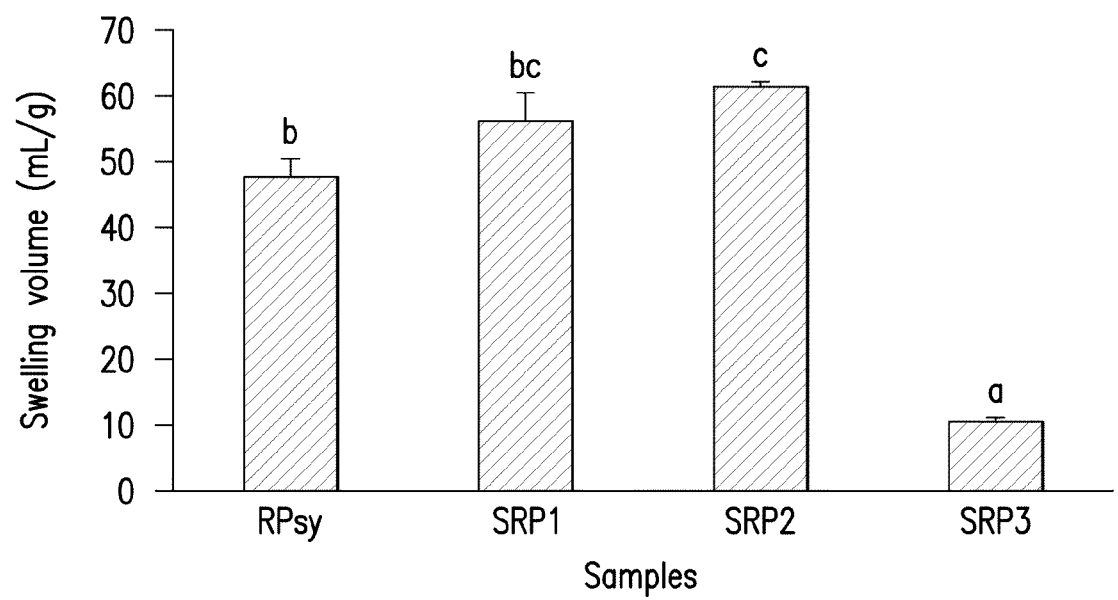
FIG. 11 is a graphical representation of the swelling capacities of RPsy, SRP1, SRP2, and SRP3.

FIG. 11 is a bar graph representation of the swelling properties of sulfated derivatives SRP1, SRP2, and SRP3 compared to raw psyllium sample RPsy. A swelling volume assay was conducted to examine the water-holding capacity of psyllium polymers. The swelling properties of a polymer is an important parameter for predicting the health beneficial effects of psyllium. As can be seen in FIG. 11, SRP1 and SRP2 showed greater swelling volumes than the raw sample RPsy; however, the gels associated with samples SRP1 and SRP2 were less solid than that of the raw psyllium sample RPsy as shown in FIGS. 10A and 10B. As can be further seen by FIG. 11, the sulfated psyllium derivative SRP3 lost most of its gel forming properties having the lowest swelling volume of 10.6 ml/g.

Figure 12A:
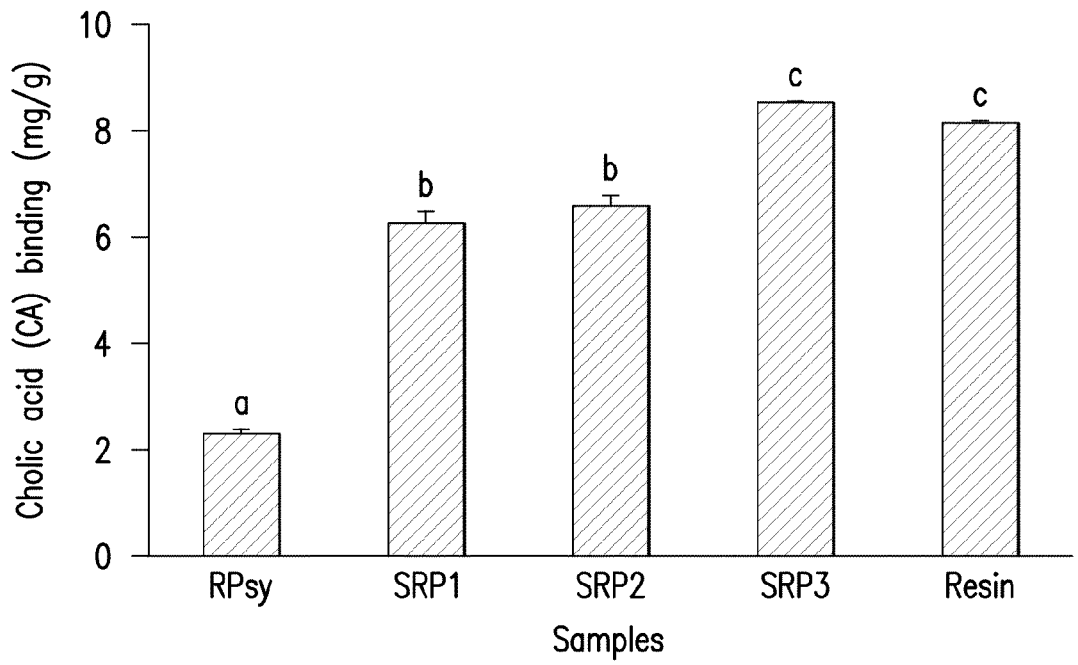
FIGS. 12A-12B are graphical representations of the bile acid-binding capacities of RPsy, SRP1, SRP2, SRP3, and resin, wherein resin represents the cholestyramine resin positive control.
Figure 12B:
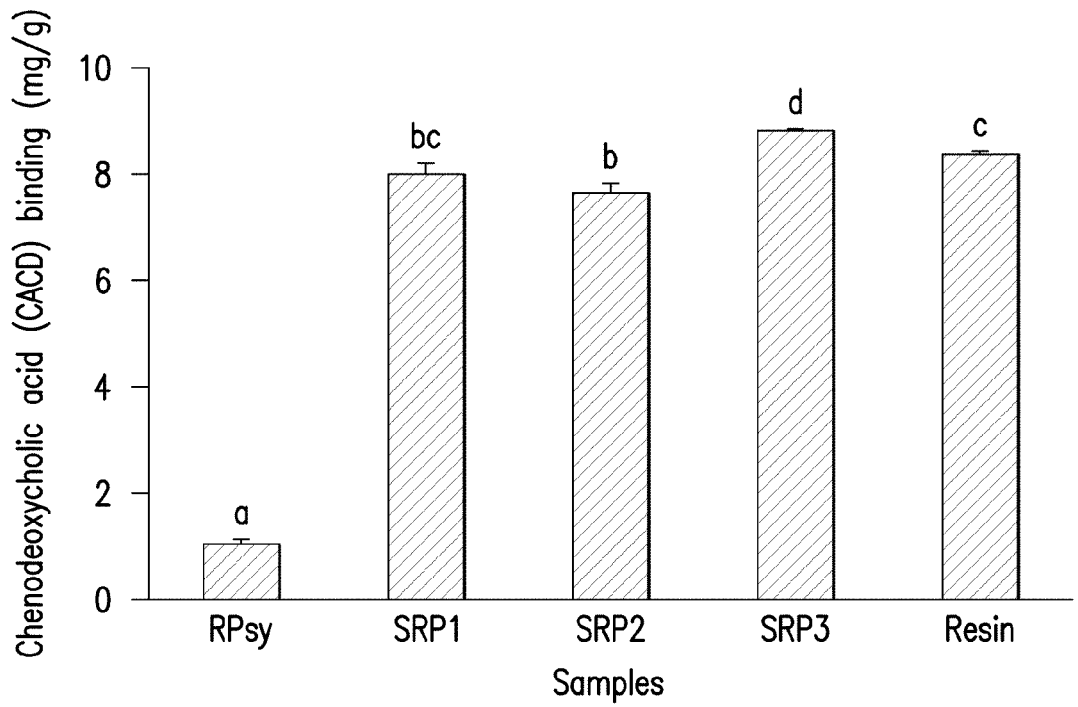

Finally, FIGS. 12A and 12B are graphical representations of the bile acid-binding capacities of the raw psyllium sample RPsy when compared with those of sulfated psyllium derivatives SRP1, SRP2, and SRP3. The bile acid-binding capacities were determined by treating 50 mg of each psyllium sample with 0.5 mL of 0.01 mol/L HCl for simulating gastric conditions. Each of the samples was incubated at 37° C. for 60 minutes with continuous shaking (50 rpm). The solutions were adjusted to pH 7.0 by adding 0.1 M NaOH, followed by the addition of 2.5 mL of 400 μmol/L bile acid (cholic acid or chenodeoxycholic acid) prepared in 0.01 M phosphate buffer (pH 7.0) for simulation of intestinal conditions. These mixtures were further incubated for another 60 minutes at 37° C. and then centrifuged for 10 minutes at 20,000 rpm. The supernatant was collected for bile acid determination from each of the RPsy, SRP1, SRP2, and SRP3 samples respectively.

Quantification of the unbound bile acids was conducted using a commercial kit from Sigma Aldrich (St. Louis, Mo.). The final assay mixture was added with 100 μL of supernatant or bile acid standards, 125 μL of 1.22 mmol/L nicotinamide adenine dinucleotide, 12 μL of 5 mmol/L nitro blue tetrazolium salt, 100 μL of 625 units per L 3-α hydroxysterol dehydrogenase, and 100 μL of 625 units/L diphorase. The respective mixtures were incubated for 60 minutes at ambient temperature. Following incubation, 1004 of 1.33 mol/L of phosphoric acid was added to terminate the reaction and the absorbance of each reaction mixture was measured at 530 nm indicating the amount of unbound acid.

Sulfated psyllium derivatives SRP1, SRP2, and SRP3 were examined and compared against the raw psyllium sample RPsy and the positive control cholestyramine resin for their individual bile acid-binding capacities against cholic acid (CA) in FIG. 12A and chenodeoxycholic acid (CDCA) in FIG. 12B. As shown in FIGS. 12A and 12B, each of the sulfated psyllium samples SRP1, SRP2, and SRP3 had significantly higher bile-binding capacities against both tested bile acids on a per as is weight basis.

Specifically, FIGS. 12A and 12B show that sulfated derivative SRP3 had the greatest binding capacity against cholic acid and chenodeoxycholic acids with a 3.5-fold and 8.8-fold greater binding capacity of that of the raw psyllium sample RPsy, respectively. Taken together, the bile acid-binding capacity shown in FIGS. 12A and 12B demonstrate that bile acid increases with sulfation.

It will be understood that the Specification and Examples are illustrative of the present invention and that other embodiments within the spirit and scope of the invention will suggest themselves to those skilled in the art.

Although this invention has been described in connection with specific forms and embodiments thereof, it would be appreciated that various modifications other than those discussed above may be resorted to without departing from the spirit or scope of the invention as defined in the appended claims. For example, equivalents may be substituted for those specifically described, and in certain cases, particular applications of steps may be reversed or interposed all without departing from the spirit or scope for the invention as described in the appended claims.

What is being claimed is:

1. A method for preparing a purified sulfated psyllium derivative having enhanced morphological and rheological properties, water intake capacities, swelling volumes and in-vitro bile acid-binding abilities, comprising the steps of:
    (a) soaking a sample of psyllium in an effective amount of a first organic solvent to form a first mixture containing psyllium;
    (b) dissolving an effective amount of sulfating agent chlorosulfonic acid (ClSO$_3$H) in an effective amount of a second organic solvent to form a second mixture;
    (c) combining said first mixture and said second mixture to initiate a reaction and form a reaction mixture, adding an effective amount of pyridine for every mole of sulfating agent used in the reaction, and stirring said reaction mixture for at least 3 hours at a temperature of approximately 60° C.;
    (d) adding an effective amount of water to said reaction mixture to terminate said reaction;
    (e) adding an effective amount of a basic solution to said reaction mixture to form a neutralized mixture;
    (f) adding an effective amount of ethanol to said neutralized mixture to form a sulfated psyllium derivative precipitate and supernatant and centrifuging to separate the precipitate and supernatant,
    (g) re-dissolving said precipitate in water to obtain a suspension and dialyzing said suspension for an amount of time to remove salt and other low molecular weight chemicals to obtain a dialyzed suspension,
    (h) adding an effective amount of ethanol to said dialyzed suspension to form a second sulfated psyllium derivative precipitate and supernatant and centrifuging to separate the second precipitate and second supernatant,
    (i) removing said second supernatant and collecting said second precipitate, wherein said second precipitate contains said purified sulfated psyllium derivate, and
    (j) drying said second precipitate to obtain said purified sulfated psyllium derivative.

2. The method as recited in claim 1, wherein the step (g) of dialyzing said suspension further includes the step of performing dialysis for at least 72 hours.

3. The method as recited in claim 1, wherein the step (g) of dialyzing said suspension further includes the step of concentrating said suspension to an effective volume under reduced pressure.

4. The method as recited in claim 1, wherein the step (i) of removing said second supernatant includes washing said second precipitate at least once with effective amounts of ethanol and acetone.

5. The method as recited in claim 1, wherein the step (j) of drying said second precipitate for obtaining said purified sulfated psyllium derivative includes drying said second precipitate under nitrogen.

6. The method as recited in claim 1 wherein said first organic solvent is an amide.

7. The method as recited in claim 6 wherein said amide is dry dimethylformamide (dDMF).

8. The method as recited in claim 1 wherein said second organic solvent is selected from the functional groups consisting of amides and amines.

9. The method as recited in claim 8 wherein when said second organic solvent is an amide, said second organic solvent is dimethylformamide (DMF).

10. The method as recited in claim 8 wherein when said second organic solvent is an amine, said second organic solvent is pyridine.

11. A method for preparing purified sulfated psyllium derivative having enhanced morphological and rheological properties, water intake capacities, swelling volumes and in-vitro bile acid-binding abilities, comprising the steps of:
 (a) soaking a sample of psyllium in an effective amount of dry dimethylformamide (dDMF) to form a first mixture containing psyllium;
 (b) dissolving an effective amount of sulfating agent chlorosulfonic acid ($ClSO_3H$) in an effective amount of dimethylformamide (DMF) to form a second mixture;
 (c) combining said first mixture and said second mixture to initiate a first reaction and form a first reaction mixture, adding an effective amount of pyridine for every mole of sulfating agent used in the reaction mixture, and stirring said first reaction mixture for approximately 3 hours at a temperature of approximately 60° C.;
 (d) adding an effective amount of water to terminate said first reaction;
 (e) adding an effective amount of sodium hydroxide to said first reaction mixture to form a first neutralized mixture;
 (f) adding an effective amount of ethanol to said first neutralized mixture to form a first sulfated psyllium derivative precipitate and first supernatant and centrifuging to separate the first precipitate and first supernatant and collecting said first supernatant;
 (g) preparing a second sample of psyllium from raw psyllium;
 (h) soaking said second sample of psyllium in an effective amount of said dry dimethylformamide (dDMF) to form a third mixture;
 (i) dissolving an effective amount of sulfating agent chlorosulfonic acid ($ClSO_3H$) in an effective amount of dimethylformamide (DMF) for forming a fourth mixture;
 (j) combining said third mixture and said fourth mixture to initiate a first reaction and form a first reaction mixture and adding an effective amount of pyridine for every mole of sulfating agent used in the reaction mixture and stirring said second reaction mixture for approximately 3 hours at a temperature of approximately 60° C.;
 (k) adding an effective amount of water to terminate said second reaction;
 (l) adding an effective amount of sodium hydroxide to said second reaction mixture to form a second neutralized mixture;
 (m) adding an effective amount of ethanol to said second neutralized mixture to form a second sulfated psyllium derivative precipitate and second supernatant and centrifuging to separate the second precipitate and second supernatant and collecting said second supernatant;
 (n) combining said first supernatant and second supernatant to obtain a combined supernatant, and
 (o) adding an effective amount of ethanol to said combined supernatant to form a final purified sulfated psyllium derivative precipitate and final supernatant and centrifuging to separate the final precipitate and final supernatant;
 (p) washing said final precipitate with ethanol and acetone and drying said final precipitate to obtain said purified sulfated derivative therefrom.

12. The method as recited in claim 11, wherein the step (k) of combining said third mixture and said fourth mixture to initiate said second reaction and form said second reaction mixture is followed by the step of stirring said second reaction mixture for approximately 4 hours at a temperature of approximately 60° C.

13. The method as recited in claim 11, wherein the step of washing said final precipitate includes the step of washing said final precipitate at least once with ethanol and acetone.

14. The method as recited in claim 11 wherein the step of drying said final precipitate for obtaining a purified sulfated psyllium derivative includes drying said final precipitate under nitrogen.

* * * * *